United States Patent
Kocinska et al.

(10) Patent No.: US 10,517,810 B2
(45) Date of Patent: Dec. 31, 2019

(54) ORAL CARE COMPOSITIONS HAVING HIGH WATER CONTENT AND MICRO ROBUSTNESS

(71) Applicant: Colgate-Palmolive Company, New York, NY (US)

(72) Inventors: Agnieszka Kocinska, Basel (CH); Pierre Lambert, Bottmingen (CH)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/529,802

(22) PCT Filed: Dec. 18, 2014

(86) PCT No.: PCT/US2014/071045
§ 371 (c)(1),
(2) Date: May 25, 2017

(87) PCT Pub. No.: WO2016/099499
PCT Pub. Date: Jun. 23, 2016

(65) Prior Publication Data
US 2017/0333330 A1    Nov. 23, 2017

(51) Int. Cl.
*A61K 8/60* (2006.01)
*A61K 8/73* (2006.01)
*A61Q 11/00* (2006.01)
*A61K 8/04* (2006.01)
*A61K 8/25* (2006.01)
*A61K 8/34* (2006.01)

(52) U.S. Cl.
CPC ............. *A61K 8/731* (2013.01); *A61K 8/042* (2013.01); *A61K 8/25* (2013.01); *A61K 8/345* (2013.01); *A61K 8/60* (2013.01); *A61K 8/73* (2013.01); *A61Q 11/00* (2013.01); *A61K 2800/28* (2013.01); *A61K 2800/30* (2013.01); *A61K 2800/48* (2013.01); *A61K 2800/92* (2013.01)

(58) Field of Classification Search
CPC ...................................................... A61K 8/731
See application file for complete search history.

(56) References Cited

U.S. PATENT DOCUMENTS

| | | | |
|---|---|---|---|
| 5,582,816 A | 12/1996 | Mandanas et al. | |
| 5,695,746 A * | 12/1997 | Garlick, Jr. | A61K 8/34 424/49 |
| 7,049,299 B2 | 5/2006 | Francois | |
| 8,506,698 B2 | 8/2013 | Blanvalet et al. | |
| 2004/0052839 A1 | 3/2004 | Archibald et al. | |
| 2012/0276023 A1 | 11/2012 | Shimohirao et al. | |
| 2013/0273128 A1 | 10/2013 | Martinetti et al. | |
| 2015/0335539 A1 | 11/2015 | Prencipe et al. | |

FOREIGN PATENT DOCUMENTS

| | | |
|---|---|---|
| EA | 001791 | 2/1999 |
| WO | 1999/044571 | 9/1999 |
| WO | WO 2001/032135 | 5/2001 |
| WO | WO 2004/071321 | 8/2004 |
| WO | WO 2009/134657 | 11/2009 |
| WO | WO 2014/100930 | 7/2014 |

OTHER PUBLICATIONS

International Search Report and Written Opinion of the International Searching Authority in International Application No. PCT/US2014/071045, dated Jun. 23, 2015.

* cited by examiner

*Primary Examiner* — Benjamin J Packard

(57) ABSTRACT

Disclosed herein are oral care compositions comprising a high water content, sorbitol, and a thickening system chosen from carrageenan and a combination of carboxymethylcellulose and xanthan. The oral care compositions may be free of glycerin and free of water-soluble stannous ions, while maintaining a Micro Robustness Index of at least about 0.75. Also disclosed herein are methods of cleaning and/or whitening the surface of a tooth comprising applying the oral care compositions disclosed herein.

16 Claims, No Drawings

ORAL CARE COMPOSITIONS HAVING HIGH WATER CONTENT AND MICRO ROBUSTNESS

BACKGROUND

Oral care compositions, such as oral care compositions comprising water, may be susceptible to bacterial growth. A high water content fosters the growth of bacteria in an oral care composition, and consequently shortens the shelf-life of the composition, resulting in consumer dissatisfaction. Therefore, oral care compositions comprising a high water content may incorporate additional preservative ingredients into their formulations, such as benzyl alcohol, aldehydes, methylparaben, and propylparaben.

Additionally, many oral care compositions may comprise expensive ingredients, such as ingredients that are naturally occurring and may be limited in the environment. One such ingredient is carrageenan, which is a thickening agent that may be extracted from red seaweeds. Therefore, an oral care composition comprising a high content of carrageenan as a thickening agent may be expensive to manufacture, and it may be desirable from a cost standpoint to formulate compositions comprising suitable alternative ingredients.

Water, of course, is a cost-effective ingredient, and therefore maximizing its content in an oral care composition's formulation may decrease the cost associated with producing that formulation, as the content of other, more expensive, ingredients may consequently by replaced by the increased water content. Accordingly, it is desirable to increase the water content of a composition without adversely affecting the composition's micro robustness, or ability to inhibit bacterial growth. Furthermore, it is desirable to increase the water content of a composition without the need to incorporate additional preservative ingredients into the formulation.

Arriving at the ideal water content, however, can be complicated when formulating oral care compositions. Reducing the level of water, and optionally replacing some or all of the removed water with a humectant, for example, may create problems in obtaining acceptable theology and thickening properties in the composition. When water, which is a highly polar solvent, is removed, conventional thickening agents, such as carboxymethylcellulose, tend to gel up inadequately. Such formulations have been shown to exhibit progressive thickening over time, which prolongs the time period to reach a theological steady state, or even prevents the dentifrice from reaching a rheological steady state altogether. If a formulation routinely increases in viscosity over time, dispensing of the formulation will become difficult, which will likely result in consumer dissatisfaction.

One method known in the art for increasing the water content while improving micro robustness involves the addition of water soluble stannous ions to an oral care composition. The stannous ions may be chosen from the group consisting of stannous chloride, stannous pyrophosphate, stannous formate, stannous acetate, stannous gluconate, stannous lactate, stannous tartrate, stannous oxalate, stannous malonate, stannous citrate, stannous ethylene glyoxide, and mixtures thereof. Stannous ions, however, such as $SnCl_2$, may be astringent compounds having a poor taste that would be unpleasant to a consumer.

Accordingly, it is desirable to formulate an oral care composition that is cost-efficient, has a high water content, desirable rheological properties, and maintains high micro robustness while being free of stannous ions.

SUMMARY

Disclosed herein is a composition, such as an oral care composition, having a high water content and comprising sorbitol and a thickening system chosen from carrageenan and a combination of xanthan and carboxy methyl cellulose (CMC). The oral care composition may be a gel or paste. In certain embodiments, the composition is free of glycerin. In certain embodiments, the composition is free of stannous ions. The compositions disclosed herein may have a Micro Robustness Index (MRI) of greater than about 0.75, such as greater than about 0.80, greater than about 0.85, greater than about 0.90, greater than about 0.95, or equal to about 1.0. In certain embodiments, the composition may comprise at least about 40% total formula water, such as at least about 45% total formula water, at least about 47% total formula water, at least about 50% total formula water, at least about 52% total formula water, at least about 55% total formula water, or at least about 60% total formula water. In certain exemplary embodiments, the oral care composition may comprise at least about 20 sorbitol.

In certain embodiments, the oral care composition may be a whitening composition. Such whitening composition may comprise at least one abrasive, such as, for example, from about 10% to about 50% of a silica abrasive, such as about 15% to about 30% or about 20% of a silica abrasive. In certain embodiments, the composition disclosed herein comprises more than about 10% silica abrasive, such as more than about 12% or more than about 15% abrasive.

Also disclosed herein are methods for cleaning the surface of a tooth comprising applying a composition comprising at least about 40% total formula water, sorbitol, and a thickening system chosen from carrageenan and a combination of xanthan and carboxymethyl cellulose (CMC), wherein the composition is substantially free of glycerin and substantially free of stannous ions, and wherein the composition has an MRI of greater than about 0.75.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiments is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Disclosed herein are oral care compositions comprising at least about 40% total formula water, sorbitol, and a thickening system chosen from carrageenan and a combination of xanthan and carboxymethyl cellulose, wherein the oral care compositions are substantially free of glycerin, substantially free of water-soluble stannous ions, and have a Micro Robustness index of at least about 0.75. In certain embodiments, the oral care compositions disclosed herein are free of antibacterial agents. In certain embodiments, the oral care compositions disclosed herein are free of preservatives.

The compositions disclosed herein have a total formula water content of at least about 40%, such as at least about 45%, at least about 47% total formula water, at least about 50% total formula water, at least about 52% total formula water, at least about 55% water, or at least about 60% total formula water. As used herein, "total formula water" refers to the total content of water, including any free water added and all water contained in any ingredients. As one skilled in the art would appreciate, water may be found in added ingredients. For example, according to certain embodiments, sorbitol may be added to compositions of the invention, such as, for example, at least about 20% sorbitol. In certain embodiments wherein sorbitol is added to compositions of the invention, it may be added as raw material, for example a raw material that is present as a 70% sorbitol solution. Accordingly, in a 70% sorbitol solution, about 30% of the sorbitol solution may comprise water that contributes to the total formula water of the composition. Therefore, in certain embodiments, less than about 40% free water may be added to a composition according to the invention, but when additional ingredients are added, such as, for example, at least about 20% of a 70% sorbitol solution, the total formula water of the composition may then increase to at least about 40%. Purely by way of illustration, a formulation may comprise about 35% free water and about 25% of a 70% sorbitol solution (i.e., about 7.5% water). Assuming no other ingredients in the formulation contain water, such a formulation would contain about 42.5% total formula water (35%+ 7.5%).

In addition to at least about 40% total formula water, the oral care compositions disclosed herein comprise sorbitol as a humectant. A humectant may be useful, for example, to prevent hardening of a toothpaste or gel upon exposure to air. In certain exemplary embodiments, the sorbitol is a 70% sorbitol solution. The sorbitol may be present in the composition in an amount of at least about 20%, such as at least about 22%, at least about 24%, at least about 25%, at least about 30%, or at least about 35%. It is understood that, as used herein, if a composition comprises an amount of sorbitol, such as at least about 20% sorbitol, the sorbitol may be present as a raw material rather than pure sorbitol. Accordingly, for a composition comprising at least about 20% sorbitol in certain exemplary embodiments wherein the sorbitol is a 70% sorbitol solution, approximately 30% of the sorbitol may comprise water, and the sorbitol raw material may also comprise a percentage of other, non-sorbitol impurities. Accordingly, the amount of pure sorbitol in the composition may, in certain embodiments, be at least about 3%, such as at least about 6%, at least about 8%, at least about 10%, or at least about 12%. The composition may further comprise at least one humectant in addition to sorbitol. Any orally-acceptable humectant may be used, including for example, xylitol, propylene glycols, polypropylene glycols, and polyethylene glycols (PEGs), such as PEG 600.

In certain embodiments, the oral care compositions disclosed herein are substantially free of glycerin as a humectant. As used herein, the term "substantially free of glycerin" means about 0% by weight of glycerin or are amount of glycerin that is so low as to not have a reasonable chemical effect on the formulation.

The oral care compositions disclosed herein further comprise at least one thickening system. The thickening system may be useful, in part, to give a desired consistency and/or mouth feel to the composition. Any orally-acceptable thickening agent may be used in the thickening system, including, for example carbomers also known as carboxyyinyl polymers, carrageenans, also known as Irish moss, cellulosic polymers such as hydroxyethyl cellulose, CMC, and salts thereof, such as CMC sodium. Other exemplary thickening agents that may be mentioned include natural gums such as karaya, xanthan, gum arabic and tragacanth, colloidal magnesium aluminum silicate, colloidal silica, alginates, bentonite and other natural clays and synthetic inorganic clays, and the like. At least one additional thickening agent may be optionally present in the composition in a total amount ranging from about 0.01% to about 15%, such as from about 0.1% to about 10%, or from 0.2% to about 5%, by weight of the composition. In one embodiment, the at least one thickening system comprises carrageenan. In one embodiment, the at least one thickening system comprises a combination of CMC present in an amount of about 0.6% about xanthan present in amount of about 0.65%.

As one skilled in the art would recognize, properties of CMC may depend on the chain length of its cellulose backbone structure. Accordingly, in certain embodiments, use may be made of CMC comprising a backbone ranging from 8 to 12 cellulose units, such as 8 cellulose units (CMC8), 9 cellulose units (CMC9), or 12 cellulose units (CMC12), CMC may be present in the oral care compositions disclosed herein in an amount ranging from about 0.1% to about 1.0%, such as about 0.1% to about 0.7%, or about 0.2% to about 0.65%.

The xanthan gum is polysaccharide having a molecular weight of about 1,000,000 to about 10,000,000. Xanthan has a primary structure consisting of regular repeating units, each containing five sugars: two glucose, two mannose, and one glucuronic acid. The main chain is built up of β-D-glucose units linked through the 1- and 4-positions, i.e, a chemical structure same as cellulose. A three-sugar side chain is linked to the 3-position of every other glucose residue in the main chain. About half of the terminal D-mannose residues contain a pyruvic acid residue linked to the 4- and 6-positions. Xanthan may be present in the oral care compositions disclosed herein in an amount ranging from about 0.1% to about 1.0%, such as about 0.1% to about 0.7% or about 0.2% to about 0.6%.

In certain embodiments, the at least one thickening system comprises carrageenan. In certain embodiments, the carrageenan may be chosen from at least one of beta-, iota-, kappa-, and lambda-type carrageenan. The at least one carrageenan may be present in the oral care composition in an amount ranging from about 0.01% to about 5.0%, such as from about 0.05% to 1.1%, by weight. In certain embodiments, the oral care composition disclosed herein is substantially free of carrageenan.

In general, it is known that increasing the water content in a formulation decreases the micro robustness, i.e., susceptibility to microbial attack. A Micro Robustness Index (MRI) may be calculated to indicate the efficacy of the formulation at deterring microbial contamination. For the purposes of the present disclosure, a composition is considered to have adequate micro robustness if the MRI is at least about 0.75. In certain embodiments disclosed herein, the composition has an MRI ranging from about 1.0 to about 0.75, such as, for example, from about 0.95 to about 0.80, or from about 0.90 to about 0.85. In certain embodiments, the MRI is greater than about 0.75, such as greater than about 0.80, greater than about 0.85, greater than about 0.90, greater than about 0.95, or is equal to about 1.0.

In order to assess the MRI of a composition, a sample of the composition may challenged with a certain quantity of various bacteria. For example, in certain embodiments, a sample formulation may be exposed to microorganisms including the following: *Burkholderia cepacia*; *Enterobacter cloacae*; *Escherichia coli*; *Klebsiella oxytoca*; *Klebsiella pneumoniae*; *Serratia marcescens*; *Providencia rettgeri*; *Pseudomonas aeruginosa*; *Pseudomonas putida*; bacteria kill log that is measured at various time points (e.g., 4, 6, and 24 hours) over a 2$ hour period. The maximum kill would be a 7 log reduction; therefore, the maximum area under the curve (AUC) would be 148 (7×24). Accordingly, an AUC of 148 is given an index of 100. The MRI is the ratio between the index of the AUC of the sample composition and the benchmark index of 100. An MRI of 1.0 indicates that the two AUC are the same. The higher the MRI, the greater the micro robustness of the formulation; to the contrary, the lower the MRI, the lower the micro robustness of the formulation. It has been observed that a composition exhibiting an MRI lower than about 0.75 may exhibit negative microbial issues, for example at the manufacturing level.

In certain embodiments disclosed herein, the oral care compositions may be substantially free of water-soluble stannous ions, while still maintaining an MRI value of at least about 0.75. For example, in certain embodiments, the oral care composition disclosed herein is substantially free of water-soluble stannous ions and has an MRI of at least about 0.80, at least about 0.85, at least about 0.90, at least about 0.95, or equal to 1.0. Although it is known that stannous ions may impart micro robustness to a composition, they also may be astringent compounds having a poor taste, and thus are commercially undesirable. Accordingly, in embodiments of the invention, the oral care composition is substantially free of stannous ions chosen, for example, from stannous chloride, stannous pyrophosphate, stannous formate, stannous acetate, stannous gluconate, stannous lactate, stannous tartrate, stannous oxalate, stannous malonate, stannous citrate, stannous ethylene glyoxide, and mixtures thereof. As used herein, "substantially free of water-soluble stannous ions" indicate that there are about 0% by weight of water-soluble stannous ions in the composition or that the amount of water-soluble stannous ions is so low as to not have a reasonable chemical effect on the composition.

In certain embodiments disclosed herein, the oral care compositions may further comprise at least one abrasive. Abrasives in oral care compositions are responsible for physically scrubbing the external surfaces of the teeth in order to remove organic biofilm, or pellicle, formed by salivary proteins, bacteria, and bacterial byproducts. Pellicle may also be stained and discolored by foods, drinks, tobacco smoke, and bacteria. Such physical removal of the stained pellicle is a simple and effective means of removing the undesirable surface staining and discoloration, and thereby effectively whitening teeth surfaces. Further, such physical removal of the pellicle also removes plaque bacteria on the pellicle surface, thereby minimizing the potential for gingivitis, periodontitis, and caries formation. Accordingly, abrasives may be desirable in an oral care composition for their whitening and oral care effects. However, oral care compositions should not have such high concentrations of abrasives that damage to the enamel or tissue may result. As such, it is desirable to develop oral care compositions to optimize the cleaning and whitening effects, while minimizing any potential abrasiveness damage. Preferably, such oral compositions should have a high pellicle cleaning ratio (PCR), but a low degree of dental abrasion, which is measured as radioactive dental abrasion (RDA). In certain exemplary embodiments, the oral care compositions disclosed herein may be characterized by a PCR value of at least about 90, such as at least about 95, at least about 100, or at least about 102. In certain exemplary embodiments, the oral care compositions disclosed herein may be characterized by an RDA value of less than about 200, such as less than about 150, less than about 130, less than about 125, or less than about 120.

Any orally acceptable abrasive can be used, but type, fineness (particle size) and amount of abrasive should be selected so that tooth enamel is not excessively abraded in normal use of the composition. Suitable abrasives include without limitation silica, for example in the form of silica gel, hydrated silica or precipitated silica, precipitated calcium carbonate, alumina, insoluble phosphates, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate and insoluble sodium polymetaphosphate. The at least one abrasive may be present in an abrasive effective total amount, such as an amount ranging from about 5% to about 70%, for example about 10% to about 50% or about 15% to about 30% by weight of the composition. In certain embodiments, the abrasive is a silica abrasive present in an amount of about 20%. Average particle size of an abrasive, if present, generally ranges from about 0.1 µm to about 30 µm, for example about 1 µm to about 20 µm or about 5 µm to about 15 µm.

Other additional ingredients may be added to the oral care composition as desired. Among potential additional ingredients for inclusion into compositions disclosed herein, mention may be of, for example, whiteners and bleaching agents, antimicrobials, bicarbonate salts, pH modifying agents, foam modulators, viscosity modifiers, surfactants, sweeteners, flavorants, and colorants.

The compositions disclosed herein may further comprise at least one tooth whitening or tooth bleaching agent. Suitable tooth whitening and bleaching agents may include at least one of peroxides, metal chlorites, and persulfates. Peroxides may include at least one of hydroperoxides, hydrogen peroxide, peroxides of alkali and alkaline earth metals, organic peroxy compounds, and peroxy acids. Peroxides of alkali and alkaline earth metals include lithium peroxide, potassium peroxide, sodium peroxide, magnesium peroxide, calcium peroxide, barium peroxide, and mixtures thereof. Other peroxides include perborate, urea peroxide, and mixtures thereof. Suitable metal chlorites may include calcium chlorite, barium chlorite, magnesium chlorite, lithium chlorite, sodium chlorite, and potassium chlorite. In certain embodiments, tooth whitening or tooth bleaching ingredients may be added in effective amounts, such as from about 1% to about 20% by weight based on the total weight of the composition.

In certain embodiments, the oral care compositions disclosed herein may further comprise at least one antimicrobial agent. Exemplary antimicrobial agents may include zinc citrate, zinc oxide, stannous chloride, tetrahydrocurcumin, cetylpyridinium chloride and triclosan. In certain embodiments, for example, at least one antimicrobial agent may be present in a composition at a concentration ranging from about 0.025 ppm to about 100 ppm. Various compositions also contain compounds or components with antibacterial properties, for example to reduce the formation of plaque on the tooth surfaces.

In certain embodiments, at least one bicarbonate salt may be added to the oral care compositions disclosed herein. At least one bicarbonate salt may be useful to impart a "clean feel" to teeth and gums due to of and release of carbon dioxide. Any orally acceptable bicarbonate can be used, including without limitation alkali metal bicarbonates, such as sodium and potassium bicarbonates, ammonium bicarbonate and the like. One or more bicarbonate salts are optionally present in a total amount ranging from about 0.1% to about 50%, such as about 1% to about 20%, by weight of the composition.

In certain embodiments, the composition comprises at least one pH modifying agent. pH modifying agents may include acidifying agents to lower pH, basifying agents to raise pH, and buffering agents to control pH within a desired range. For example, one or more compounds selected from acidifying, basifying and buffering agents can be included. Any orally acceptable pH modifying agent can be used, including without limitation carboxylic, phosphoric and sulfonic acids, acid salts (such as monosodium citrate, disodium citrate, and monosodium malate), alkali metal hydroxides such as sodium hydroxide, carbonates such as sodium carbonate, bicarbonates, sesquicarbonates, borates, silicates, phosphates (such as monosodium phosphate, trisodium phosphate, and pyrophosphate salts), imidazole and the like. The at least one pH modifying agent may be optionally present in a total amount effective to maintain the composition in an orally acceptable pH range.

In certain embodiments, the compositions disclosed herein may further comprise at least one foam modulator. At least one foam modulator may be useful to increase the amount, thickness, or stability of foam generated by the composition upon agitation. Any orally acceptable foam modulator can be used, including for example polyethylene glycols (PLCs), also known as polvoxyethylenes. High molecular weight PEC is are suitable, including those having an average molecular weight ranging from about 200,000 to about 7,000,000, such as for example about 500,000 to about 5,000,000, or about 1,000,000 to about 2,500,000. At least one foam modulator may be present in the oral care composition in a total amount ranging from about 0.1% to about 10%, such as from about 0.2% to about 5%, or from about 0.25% to about 2%, by weight of the composition.

In certain embodiments, the compositions disclosed herein may further comprise at least one viscosity modifier. At least one viscosity modifier may be useful for example to inhibit settling or separation of ingredients or to promote redispersibility upon agitation of a liquid composition. Any orally acceptable viscosity modifier can be used, including for example mineral oil, petrolatum, clays and organomodified clays, silica and the like. The at least one viscosity modifier may be optionally present in the oral care composition in a total amount ranging from about 0.01% to about 10%, such as from about 0.1% to about 5%, by weight of the composition.

In certain embodiments, the oral care compositions disclosed herein comprises at least one surfactant. At least one surfactant may be useful to improve the compatibility of the other components of the composition and thereby provide enhanced stability, to help in cleaning the dental surface through detergency, and to provide foam upon agitation, for example during brushing with oral care compositions as disclosed herein. Any orally acceptable surfactant, most of which are anionic, nonionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, tartrates and the like. Illustrative examples of these and other classes include sodium lauryl sulfate, sodium coconut monoglyceride sultanate, sodium lauryl sarcosinate, sodium lauryl isoethionate, sodium laureth carboxylate, and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation derivatives of $C_{8-20}$ aliphatic secondary and tertiary amines having an anionic group such as carboxylate, sulfate, sulfonate, phosphate or phosphonate. Examples include cocoamidopropyl betaine, N-alkyldiaminoethylglycines (N-laurylaminoethylglycine, N-myristyldiethylglycine, etc.), N-alkyl-N-carboxymethylammonium betaine, 2-alkyl-1-hydroxyethylimidazoline betaine sodium and lauryldimethylaminoacetic acid betaine. The at least one surfactant may be present in the oral care composition in a total amount ranging from about 0.01% to about 10%, such as from about 0.05% to about 5%, or from about 0.1% to about 2%, by weight of the composition.

In certain embodiments, the oral care compositions disclosed herein further comprise at least one sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, acesulfame potassium, glycyrrhizin, perillantine, thaumatin aspartame, neotame, saccharin and salts thereof, dipeptide-based intense sweeteners, cyclamates and the like. The at least one sweeteners may be present in the oral care composition in a total amount depending on the particular sweetener or sweeteners selected, but typically may range from about 0.005% to about 5% by weight of the composition.

In certain embodiments, the oral care compositions disclosed herein further comprise at least one flavorant, useful for example to enhance taste of the composition. Any orally acceptable natural or synthetic flavorant can be used, including without limitation vanillin, sage, marjoram, parsley oil, spearmint oil cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming evicts. Such ingredients illustratively include menthol, menthol acetate, menthyl lactate, camphor, eucalyptus oil, eucalyptol, anethole eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthane glycerol acetal (MGA) and the like. The at least one flavorant may be present in the oral care composition in a total amount ranging from about 0.01% to about 5%, such as from about 0.1% to about 2.5%, by weight of the composition.

In certain embodiments, the oral care compositions disclosed herein further comprise at least one colorant. Colorants may include pigments, dyes, lakes, strips and agents imparting a particular luster or reflectivity such as pearling agents. A colorant can serve a number of functions, including, for example, to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally-acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. The at least one colorant may be present in the oral care composition in a total amount ranging from about 0.001% to about 20%, such as from about 0.01% to about 10%, or from about 0.1% to about 5%, by weight of the composition.

Oral care compositions may also be formulated with additional optional ingredients, such as, for example anticaries agents, antibacterial agents, anticalculus, tartar control agents, anti-plaque agents, breath freshening agents, anti-inflammatory agents, enzymes, vitamins, and anti-adhesion agents.

In certain embodiments, the oral care compositions disclosed herein may further comprise at least one anticaries agent, such as an orally acceptable source of fluoride ions. Suitable sources of fluoride ions include fluoride, monofluorophosphate and fluorosilicate salts, as well as amine fluorides, including olaflur (N'-octadecyltrimethylendiamine-N,N,N'-tris(2-ethanol)-dihydrafluoride). As an anticaries agent, at least one fluoride-releasing salt may be present in an amount providing a total of about 100 to about 20,000 ppm, such as about 200 to about 5,000 ppm, or about 500 to about 2,500 ppm, fluoride ions. Where sodium fluoride or monofluorophosphate is the sole fluoride-releasing salt present, an exemplary amount ranging from about 0.01% to about 5%, such as from about 0.05% to about 1% or about 0.1% to about 0.5%, sodium fluoride by weight may be present in the oral care composition.

In certain embodiments, the oral care compositions disclosed herein do not comprise any antibacterial agents. Nevertheless, in certain embodiments, it may be possible for an oral care composition as disclosed herein to comprise at least one antibacterial agent. Such antibacterial agents may include, for example, halogenated diphenylether compounds, cetyl pyridinium chloride, polyphenols, phenolic compounds, stannous ions, zinc ions, and the like. A non-limiting example of a halogenated diphenylether compound is triclosan.

In certain embodiments, the oral care compositions disclosed herein do comprise any preservative agents. Nevertheless, in certain embodiments, it may be possible for an oral care composition as disclosed herein to comprise at least one preservative agent. Such preservative agents may include, for example, parabens such as methylparaben and propylparaben.

In certain embodiments, the oral care compositions disclosed herein further comprise at least one orally-acceptable anticalculus agent. Suitable anticalculus agents may include without limitation phosphates and polyphosphates (for example pyrophosphates), polyaminopropanesulfonic acid (AMPS), zinc citrate trihydrate, polypeptides such as polyaspartic and polyglutamic acids, polyolefin sulfonates, polyolefin phosphates, diphosphonates such as azacycloalkane-2,2-diphosphonates (e.g., azacycloheptane-2,2-diphosphonic acid, N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts illustratively include monobasic, dibasic and tribasic sodium phosphates, sodium tripolyphosphate, tetrapolyphosphate, mono-, di-, tri- and tetrasodium pyrophosphates, disodium dihydrogen pyrophosphate, sodium trimetaphosphate, sodium hexametaphosphate and the like, wherein sodium can optionally be replaced by potassium or ammonium. Other useful antiealculus agents include anionic polycarboxylate polymers. The anionic polycarboxylate polymers contain carboxyl groups on a carbon backbone and include polymers or copolymers of acrylic acid, methacrylic, and maleic anhydride. Non-limiting examples include polyvinyl methyl etherimaleic anhydride (PVME/MA) copolymers, such as those available under the Gantrez™ brand from ISP. Still other useful anticalculus agents may include sequestering agents, such as hydroxycarboxylic acids including citric, fumaric, malic, glutaric and oxalic acids and salts thereof, and aminopolycarboxylic acids such as ethylenediaminetetraacetic acid (EDTA). The at least one anticalculus agent may be present in the oral care composition in an anticalculus effective total amount, which may, for example, range from about 0.01% to about 50%, such as from about 0.05% to about 25% or from about 0.1% to about 15% by weight of the composition.

In certain embodiments, the oral care compositions disclosed herein may further comprise at least one orally-acceptable zinc ion source useful, for example, as an anticalculus or breath-freshening agent. Suitable zinc ion sources include without limitation zinc acetate, zinc citrate, zinc gluconate, zinc glycinate, zinc oxide, zinc sulfate, sodium zinc citrate and the like. The at least one zinc ion source may be present in the oral care composition in a total amount ranging from about 0.05% to about 3%, such as from about 0.1% to about 1%, by weight of the composition.

In certain embodiments, the oral care compositions disclosed herein further comprise at least one orally-acceptable breath-freshening agent in a breath-freshening effective total amount. Suitable breath-freshening agents include without limitation zinc salts, such as zinc gluconate, zinc citrate and zinc chlorite, α-ionone and the like.

In certain embodiments, the oral care compositions may further comprise at least one orally acceptable antiplaque agent, including plaque disrupting agent, present in an antiplaque effective total amount. Suitable antiplaque agents include without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and chelating agents such as citric and tartaric acids and alkali metal salts thereof.

In certain embodiments, the oral care compositions disclosed herein further comprise at least one orally-acceptable anti-inflammatory agent in an anti-inflammatory effective total amount. Suitable anti-inflammatory agents include without limitation steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone.

In certain embodiments, oral care compositions disclosed herein may further comprise other ingredients such as enzymes, vitamins and anti-adhesion agents. Enzymes such as proteases can be added for anti-stain and other effects. Non-limiting examples of vitamins include vitamin C, vitamin E and analogs thereof, vitamin B5, and folk acid. In various embodiments, the vitamins may have antioxidant properties. Anti-adhesion agents may include solbrol, ficin, and quorum sensing inhibitors.

EXAMPLES

Comparative Examples 1-5

Comparative sample compositions 1-5 were prepared. In addition to water, Comparative Sample 1 comprised, inter alia, glycerin, sorbitol, xanthan and CMC8, and had an MRI of 0.88.

Comparative Sample 2 comprised, inter alia, glycerin, sorbitol, and carrageenan, and had and MRI of 0.63. Comparative Samples 3-5 comprised, inter alia, varying amounts of glycerin and water, sorbitol, xanthan, and carrageenan. Comparative Samples 3-5 reported MRI values of 0.66, 0.64, and 1.0, respectively. The formulations of Comparative Samples 1-5 are described in detail in Table 1, below.

None of Comparative Samples 2, 3, or 4 had an MRI value mater than 0.75. Although Comparative Samples 1 and 5 had MRI values greater than 0.75, both samples contained glycerin and relatively low amounts of total formula water (e.g., relatively low amounts of 70% solution sorbitol).

TABLE 1

| Ingredient | Comparative Sample 1 | Comparative Sample 2 | Comparative Sample 3 | Comparative Sample 4 | Comparative Sample 5 |
|---|---|---|---|---|---|
| 98.0-101% Kosher Glycerin - USP and EP | 17.67% | 14.73% | 13.19% | 14.73% | 17.67% |
| Sorbitol - Non-crystal - 70% Solution USP | 6.00% | 6.00% | 6.00% | 6.00% | 6.00% |
| PEG 600 | 1.50% | 1.50% | 1.50% | 1.50% | 1.50% |
| Synthetic Amorphous Silica (Sylodent VP5) | 20.00% | 20.00% | 20.00% | 20.00% | 20.00% |
| Synthetic Amorphous ppt Silica - thickener | 5.62% | 5.62% | 7.00% | 7.00% | 6.00% |
| Sodium bicarbonate - powdered | 1.99% | 1.99% | 1.99% | 1.99% | 1.99% |
| Pearl Mint Flavor | 1.20% | 1.20% | 1.20% | 1.20% | 1.20% |
| 95% Sodium Lauryl Sulfate granules | 1.20% | 1.20% | 1.20% | 1.20% | 1.20% |
| Carrageenan | — | 1.1% | — | — | — |
| Xanthan | 0.65 | — | 0.65% | 0.65% | 0.65% |
| CMC8 | 0.60 | — | 0.60% | 0.60% | 0.60% |
| Titanium dioxide | 1.00% | 1.00% | 1.00% | 1.00% | 1.00% |
| Sodium flouride | 0.32% | 0.32% | 0.32% | 0.32% | 0.32% |
| Sodium saccharin | 0.27% | 0.27% | 0.27% | 0.27% | 0.27% |
| Amorphous silica blue | 0.08% | 0.08% | 0.08% | 0.08% | 0.08% |
| Purified water | 41.91% | 45% | 45% | 43.46% | 41.52% |
| Total formula water | 43.71% | 46.8% | 46.8% | 45.26% | 43.32% |
| TOTAL | 100% | 100% | 100% | 100% | 100% |
| MRI | 0.88 | 0.63 | 0.66 | 0.64 | 1.0 |

The samples were each subjected to a Micro Robustness Test, which is a challenge test to assess the antimicrobial efficacy of a compound or compounds against a group of microorganisms. The microorganisms include the following: Burkholderia cepacia; Enterbacter cloacae; Escherichia coli; Klebsiella oxytoca; Klebsiella pneumoniae; Serratia marcescens; Providencia rettgeri; Pseudomonas aeruginosa; Pseudomonas putida; Staphylococcus aureus; and Staphylococcus saprophyticus. Sample were challenged 3 times at 30 minute intervals with an inoculum of $10^7$ bacteria from the above-listed pool. After 4, 6, and 24 hours, aliquots were tested to measure the log reduction of bacteria.

Example 6

Sample 6 comprised, inter alia, 39.09% water (47.42% total formula water), sorbitol, xanthan, and CMC8. Sample 6 was determined to have an MRI value of 1.0. The formulation of Sample 6 is described in Table 2, below.

TABLE 2

| Ingredient | Sample 6 |
| --- | --- |
| Glycerin | — |
| Sorbitol - Non-crystal - 70% Solution USP | 25.60% |
| PEG 600 | 2.00% |
| Synthetic Amorphous Silica (Sylodent VP5) | 20.00% |
| Synthetic Amorphous ppt Silica - thickener | 6.00% |
| Sodium bicarbonate - powdered | 1.99% |
| Pearl Mint Flavor | 1.20% |
| 95% Sodium Lauryl Sulfate granules | 1.20% |
| Carrageenan | — |
| Xanthan | 0.65% |
| CMC8 | 0.60% |
| Titanium dioxide | 1.00% |
| Sodium fluoride | 0.32% |
| Sodium saccharin | 0.27% |
| Amorphous silica blue | 0.08% |
| Purified water | 39.09% |
| Total formula water | 47.42% |
| TOTAL | 100% |
| MRI | 1.0 |

Sample 6 was subjected to a Micro Robustness Test as described above for. Comparative Samples 1-5.

As shown, Sample 6 comprises a relatively high total formula water content of 47.42%, while maintaining a strong MRI value of 1.0. The sample does not comprise glycerin or stannous ions, and also does not comprise carrageenan.

What is claimed is:

1. An oral care composition comprising:
   at least about 45% total formula water;
   at least about 20% of a 70% sorbitol solution; and
   at least one thickening system wherein the at least one thickening system comprises a combination of carboxymethyl cellulose and xanthan;
   wherein the composition is substantially free of glycerin and substantially free of water-soluble stannous ions,
   wherein the composition is free of additional preservatives, and
   wherein the composition has a Micro Robustness Index of at least about 0.75.

2. The oral care composition according to claim 1, wherein the oral care composition is a paste or gel.

3. The oral care composition according to claim 1, wherein the oral care composition is a whitening composition.

4. The oral care composition according to claim 1, further comprising from about 15% to about 30% of at least one abrasive.

5. The oral care composition according to claim 4, wherein the at least one abrasive is a silica abrasive.

6. The oral care composition according to claim 1, wherein the carboxymethyl cellulose has a cellulose chain length ranging from 8 to 12 cellulose units.

7. The oral care composition according to claim 6, wherein the carboxymethyl cellulose has a cellulose chain length of 8 cellulose units.

8. The oral care composition according to claim 1, wherein the carboxymethyl cellulose and xanthan are each independently present in the composition in an amount ranging from about 0.5% to about 1%.

9. The oral care composition according to claim 1, wherein the carboxymethyl cellulose is present in the composition in an amount of about 0.60% and the xanthan is present in the composition in an amount of about 0.65%.

10. The oral care composition according to claim 1, wherein the Micro Robustness Index is at least about 0.80.

11. The oral care composition according to claim 1, wherein the Micro Robustness Index is at least about 0.90.

12. The oral care composition according to claim 1, wherein the Micro Robustness Index is at least about 0.95.

13. The oral care composition according to claim 1, wherein the composition is free of additional antibacterial agents.

14. The oral care composition according to claim 1, wherein the composition further comprises at least one additional ingredient chosen from whitening and bleaching agents, bicarbonate salts, pH modifiers, surfactants, foam modulators, viscosity modifiers, sweeteners, flavorants, colorants, anticaries agents, anticalculus agents, tartar control agents, anti plaque agents, breath freshening agents, anti-inflammatory agents, enzymes, vitamins and anti-adhesion agents.

15. A method for cleaning the surface of a tooth comprising applying a composition according to claim 1.

16. The method for cleaning the surface of a tooth according to claim 15 wherein the composition further comprises at least one abrasive having a whitening effect on the surface of the tooth.

* * * * *

UNITED STATES PATENT AND TRADEMARK OFFICE
CERTIFICATE OF CORRECTION

PATENT NO. : 10,517,810 B2
APPLICATION NO. : 15/529802
DATED : December 31, 2019
INVENTOR(S) : Agnieszka Kocinska et al.

Page 1 of 1

It is certified that error appears in the above-identified patent and that said Letters Patent is hereby corrected as shown below:

In the Specification

In Column 2, Line 29, delete "abrasive." and insert -- silica abrasive. --, therefor.

In Column 3, Line 65, delete "are" and insert -- an --, therefor.

In Column 4, Line 6, delete "carboxyyinyl" and insert -- carboxyvinyl --, therefor.

In Column 7, Line 8, delete "of" and insert -- effervescence --, therefor.

In Column 7, Line 39, delete "polvoxyethylenes." and insert -- polyoxyethylenes. --, therefor.

In Column 8, Line 4, delete "tartrates" and insert -- taurates --, therefor.

In Column 8, Lines 6-7, delete "sultanate," and insert -- sulfonate, --, therefor.

In Column 8, Line 58, delete "evicts." and insert -- effects. --, therefor.

In Column 8, Line 59, after "include menthol,", delete "menthol" and insert -- menthyl --, therefor.

In Column 8, Line 65, delete "menthane" and insert -- menthone --, therefor.

In Column 12, Line 6, delete "mater" and insert -- greater --, therefor.

In Column 12, Line 55, delete "Enterbacter" and insert -- Enterobacter --, therefor.

In Column 12, Line 59, delete "Sample" and insert -- Samples --, therefor.

Signed and Sealed this
Thirty-first Day of March, 2020

Andrei Iancu
*Director of the United States Patent and Trademark Office*